United States Patent
Sada

(10) Patent No.: US 10,555,528 B1
(45) Date of Patent: Feb. 11, 2020

(54) HERBICIDAL COMPOSITION AND METHOD FOR CONTROLLING WEEDS

(71) Applicant: SUMITOMO CHEMICAL COMPANY, LIMITED, Tokyo (JP)

(72) Inventor: Yoshinao Sada, Kasai (JP)

(73) Assignee: SUMITOMO CHEMICAL COMPANY, LIMITED, Tokyo (JP)

(*) Notice: Subject to any disclaimer, the term of this patent is extended or adjusted under 35 U.S.C. 154(b) by 0 days.

(21) Appl. No.: 16/359,756

(22) Filed: Mar. 20, 2019

(51) Int. Cl.
| | |
|---|---|
| *A01N 57/20* | (2006.01) |
| *A01N 43/54* | (2006.01) |
| *A01N 43/84* | (2006.01) |
| *A01N 25/32* | (2006.01) |
| *A01N 43/38* | (2006.01) |
| *A01N 43/82* | (2006.01) |

(52) U.S. Cl.
CPC ............ *A01N 57/20* (2013.01); *A01N 25/32* (2013.01); *A01N 43/38* (2013.01); *A01N 43/54* (2013.01); *A01N 43/82* (2013.01); *A01N 43/84* (2013.01)

(58) Field of Classification Search
CPC combination set(s) only.
See application file for complete search history.

(56) References Cited

U.S. PATENT DOCUMENTS

| | | |
|---|---|---|
| 4,994,102 A | 2/1991 | Yoshido et al. |
| 5,173,103 A | 12/1992 | Yoshida et al. |
| 7,012,040 B2 | 3/2006 | Hacker et al. |
| 7,105,470 B1 | 9/2006 | Hacker et al. |
| 2004/0235665 A1 | 11/2004 | Zagar et al. |
| 2015/0024940 A1 | 1/2015 | Kim et al. |
| 2018/0007901 A1 | 1/2018 | Massa et al. |

FOREIGN PATENT DOCUMENTS

| | | | |
|---|---|---|---|
| WO | WO 03/024221 A1 | 3/2003 | |
| WO | WO 2013/154396 A1 | 10/2013 | |
| WO | WO 2016/113334 A1 | 7/2016 | |
| WO | WO 2019/030086 A2 | 2/2019 | |
| WO | WO-2019030098 A1 * | 2/2019 | ............ A01N 33/22 |

OTHER PUBLICATIONS

<http: extension.agron.iastate.edu="" weeds="" mgmt="" 2004="" ppoinjury.shtml="">Hartzler, B., "Sulfentrazone and flumioxazin injury to soybean," ISU Weed Science Online—Soybean Injury with PPO Inhibitors, Iowa State University, (Jul. 7, 2004), obtained from the Internet on Jun. 19, 2019: <http://extension.agron.iast.*

* cited by examiner

*Primary Examiner* — John Pak
(74) *Attorney, Agent, or Firm* — Birch, Stewart, Kolasch & Birch, LLP

(57) ABSTRACT

Provided is a herbicidal composition comprising a PPO inhibitor and glufosinate or its salt, wherein the weight ratio of the PPO inhibitor to glufosinate or its salt is less than 1/2,000. The herbicidal composition can effectively control weeds with reduced crop injury.

4 Claims, No Drawings

HERBICIDAL COMPOSITION AND METHOD FOR CONTROLLING WEEDS

TECHNICAL FIELD

The present invention relates to a herbicidal composition and a method for controlling weeds in a crop field.

BACKGROUND ART

Hitherto, glufosinate and its salts are used for the purpose of controlling weeds. However, a crop injury caused by glufosinate or its salts is occasionally a problem (see Patent Document 1).

A herbicidal composition comprising glufosinate or its salts and a PPO inhibitor is known to have a synergistic herbicidal activity (see Patent Document 2-6). These documents, however, do not disclose less than 1/2,000 as a weight ratio of the PPO inhibitor to glufosinate or its salt.

CITATION LIST

Patent Document

Patent Document 1: US7012040
Patent Document 2: WO2003024221
Patent Document 3: WO2016113334
Patent Document 4: WO 2013154396
Patent Document 5: WO 2019030086
Patent Document 6: U.S. Pat. No. 7,105,470

SUMMARY OF THE INVENTION

Problems to be Solved by Invention

An object of the present invention is to provide a herbicidal composition comprising glufosinate or its salt with reduced crop injury.

Means to Solve Problems

The present inventor has found out that a combined use of glufosinate or its salt and a certain amount of PPO inhibitor can reduce crop injury caused by glufosinate or its salt.

The present invention includes the following [1] to [6].
[1] A herbicidal composition comprising a PPO inhibitor and glufosinate or its salt, wherein the weight ratio of the PPO inhibitor to glufosinate or its salt is less than 1/2,000.
[2] The herbicidal composition according to [1], wherein the weight ratio of the PPO inhibitor to glufosinate or its salt is from 1/2,000,000 to 1/2,000.
[3] The herbicidal composition according to [1], wherein the PPO inhibitor is selected from the group consisting of saflufenacil, trifludimoxazin, flumioxazin, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate, sulfentrazone, lactofen, fomesafen or its salt, flumiclorac-pentyl, carfentrazone-ethyl, fluthiacet-methyl, and tiafenacil.
[4] A method for controlling weeds in a crop field comprising a step of applying a PPO inhibitor and glufosinate or its salt to the weeds or a soil of the place where the weeds are growing or will grow, wherein the weight ratio of the PPO inhibitor to glufosinate or its salt is less than 1/2,000.
[5] The method according to [4], wherein the weight ratio of the PPO inhibitor to glufosinate or its salt is from 1/2,000,000 to 1/2,000.
[6] The method according to [4], wherein the PPO inhibitor is selected from the group consisting of saflufenacil, trifludimoxazin, flumioxazin, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate, sulfentrazone, lactofen, fomesafen or its salt, flumiclorac-pentyl, carfentrazone-ethyl, fluthiacet-methyl, and tiafenacil.

The present invention can control weeds with reduced crop injury.

DESCRIPTION OF EMBODIMENTS

The herbicidal composition of the present invention (hereinafter, referred to as "present composition") comprises a PPO inhibitor and glufosinate or its salt (hereinafter, referred to as "present compounds" collectively), wherein the weight ratio of the PPO inhibitor to glufosinate or its salt is less than 1/2,000.

The method for controlling weeds of the present invention (hereinafter, referred to as "present method") comprises a step of applying the present composition or the present compounds (a PPO inhibitor and glufosinate or its salt, separately or jointly) to the weeds or a soil of the place where the weeds are growing or will grow in a crop field, wherein the weight ratio of the PPO inhibitor to glufosinate or its salt is less than 1/2,000.

PPO inhibitor is a herbicidal active ingredient known as protoporphyrinogen oxidase inhibitor, and is available from commercial sources. Example of the PPO inhbitors which can be used for the present invention include saflufenacil, trifludimoxazin, flumioxazin, ethyl [3-[2-chloro-4-fluoro-5-(1-methyl-6-trifluoromethyl-2,4-dioxo-1,2,3,4-tetrahydro-pyrimidin-3-yl)phenoxy]-2-pyridyloxy]acetate, sulfentrazone, lactofen, fomesafen or its salts, flumiclorac-pentyl, carfentrazone-ethyl, fluthiacet-methyl, tiafenacil, pyraflufen-ethyl, azafenidin, oxadiazon, oxadiargyl, cinidon-ethyl, pyraclonil, cyclopyranil, flufenpyr-ethyl, butafenacil, fluazolate, pentoxazone, oxyfluorfen, acifluorfen or its salt, aclonifen, bifenox, fluoroglycofen-ethyl. Preferable PPO inhibitors are saflufenacil and trifludimoxazin.

In the present invention, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate is a compound disclosed in the Patent Document 5 and is referred to as "compound X" hereafter. The compound X is a compound represented by the following formula (1) and can be produced according to a known process.

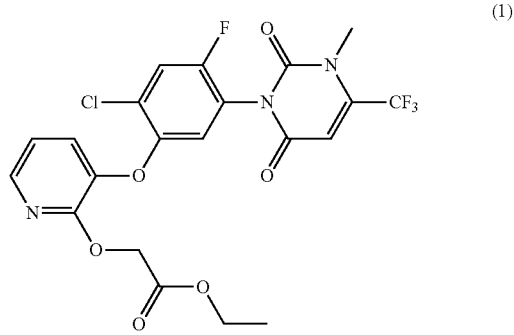 [SMILES: CCOC(=O)COc1ncccc1Oc1cc(-n2c(=O)cc(C(F)(F)F)n(C)c2=O)c(F)cc1Cl]

Glufosinate or its salt is a herbicidal active ingredient which belongs to a class of Glutamine synthase inhibitor and is described in, for example, the Patent Documents 1-7. In the present invention, glufosinate or its salt includes enantiomers and racemate. Typically, racemic glufosinate and glufosinate-P (L-glufosinate) are included. Examples of glufosinate salts which can be used for the present invention include glufosinate-ammonium, glufosinate-P-ammonium, glufosinate-sodium, and glufosinate-P-sodium. The most preferable glufosinate salt is glufosinate-ammonium.

The present composition is usually a formulation prepared by mixing the PPO inhibitor and glufosinate or its salt with a carrier such as a solid carrier and a liquid carrier, and adding auxiliary agents for formulation such as surfactant as necessary. Preferable formulation type is a soluble liquid, a suspension concentrate, a wettable powder, a water dispersible granule, a granule, or an emulsifiable concentrate. Most preferred formulation type is a soluble liquid. The present composition may be used by mixing with a formulation containing other herbicides as an active ingredient. Further, the present composition may comprise other herbicidal active ingredient(s).

The total content of the PPO inhibitor and glufosinate or its salt in the present composition is usually within a range of 0.01 to 90% by weight, preferably 1 to 80% by weight.

In addition, a weight ratio of the PPO inhibitor to glufosinate or its salt (the PPO inhibitor/glufosinate or its salt) in the present composition or in the present method is less than 1/2,000, preferably 1/2,000,000 to 1/2,000. Examples of the specific weight ratio of the PPO inhibitor to glufosinate or its salt include 1/3,000, 1/5,000, 1/10,000, 1/30,000, 1/50,000, 1/100,000, 1/300,000, 1/1,000,000, 1/3,000,000, and 1/10,000,000.

The present composition and the present method can reduce injury on crops compared to the injury of glufosinate or its salt applied alone. At the same time, the present composition and the present method can efficiently control a broad range of weeds in a crop field.

In the present method, the present composition or the present compounds may be applied to the field where crop seeds were seeded or will be seeded before, concurrently with, and/or after seeding the crop seeds treated with one or more compounds selected from the group consisting of insecticide compounds, nematicide compounds, and fungicide compounds and the like.

Examples of the insecticide compounds, nematicide compounds, and fungicide compounds which may be used in combination with the present composition or the present compounds include neonicotinoid compounds, diamide compounds, carbamate compounds, organophosphorus compounds, biological nematicide compounds, other insecticide compounds and nematicide compounds, as well as azole compounds, strobilurin compounds, metalaxyl compounds, SDHI compounds, other fungicide compounds, and plant growth regulators.

The crop field in the present invention may include a row crop field such as a peanut field, a soybean field, a corn field, a cereal field, a *sorghum* field, an oat field, a cotton field, a rapeseed field, a sugarcane field, a sunflower field, a sugar beet field. The crop field in the present invention may include a vegetable crop field such as a field for cultivating solanaceae vegetables (eggplant, tomato, green pepper, chili pepper, potato, etc.), a field for cultivating cucurbitaceae vegetables (cucumber, pumpkin, zucchini, watermelon, melon, etc.), a field for cultivating cruciferous vegetables (radish, turnip, horseradish, kohlrabi, Chinese cabbage, cabbage, mustard, broccoli, cauliflower, etc.), a field for cultivating asteraceae vegetables (burdock, crown daisy, artichoke, lettuce, etc.), a field for cultivating liliaceae vegetables (welsh onion, onion, garlic, asparagus, etc.), a field for cultivating umbelliferae vegetables (carrot, parsley, celery, parsnip, etc.), a field for cultivating chenopodiaceae vegetables (spinach, beet, etc.), a field for cultivating lamiaceae vegetables (*perilla*, mint, basil, lavender, etc.), a strawberry field, a sweet potato field, a yam field, and an aroid field, etc.

The crop field in the present invention may include a perennial crop field such as an orchard, a tea field, a mulberry field, a coffee field, a banana field, a palm field, a flowering tree farm, a flowering tree field, a planting stock field, a nursery field, a forest land, or a garden. The orchard tree in the present invention may include pomaceous fruits (apple, pear, Japanese pear, Chinese quince, quince, etc.), stone fruits (peach, plum, nectarine, Japanese apricot, yellow peach, apricot, prune, etc.), citrus fruits (citrus unshiu, orange, lemon, lime, grapefruit, etc.), nut trees (chestnut, walnut, hazelnut, almond, pistachio, cashew nut, macadamia nut, etc.), berry fruits (grape, blueberry, cranberry, blackberry, raspberry, etc.), persimmon, olive, loquat, etc.

In the present invention, the crops are not limited as long as the crops are a variety which can usually be cultivated as crops. The crops are typically corn, cotton, soybean, rapeeed, sugar beet, *sorghum*, cereals (wheat, barley, rye, and oat), and sunflower, and preferably corn, cotton and soybean.

The aforementioned crops in the present invention may be the crops producible by natural crossing, crops producible by a mutation, F1 hybrid crops, or transgenic crops (also called genetically modified crops). These crops may have more characteristics such as impartment of tolerance to different herbicides, accumulation of substances harmful to pests, reduction in sensitivity to diseases, increase in yield potential, improvement in resistance to biotic or abiotic stress factors, accumulation of substances, and improvement in preservability and processability.

The F1 hybrid crops are those which are each a first filial hybrid obtained by crossing two different varieties with each other and are usually those having characteristics superior in heterosis, that is a nature more excellent than both of the parents. The transgenic crops are those which are obtained by introducing an exogeneous gene from other organisms such as microorganisms and have characteristics like those that cannot be easily obtained by crossbreeding, mutation induction, or natural recombination in natural environments.

Examples of the technologies used to create the above crops include conventional type variety improvement; genetic recombination technologies; genome breeding technologies; new breeding technologies; and genome editing technologies. The conventional type variety improvement is specifically a technology for obtaining crops having desired properties by a spontaneous mutation and crossing. The genetic recombination technologies are technologies in which a target gene (DNA) is extracted from a certain organism (for example, microorganism) to introduce it into a genome of a different target organism, thereby new properties to the organism, and antisense technologies or RNA interference technologies for imparting new or improved characteristics by silencing other genes existing in crops. The genome breeding technologies are those improving breeding efficiency by using genome information and include DNA marker (also called genome markers or genetical markers) breeding technologies and genomic selection. For example, the DNA marker breeding is a method in which a progeny having a gene with a target and useful trait is selected from a lot of cross progenies by using a DNA marker which is a DNA sequence and is a target of the presence position of a gene with a specific useful trait on a genome. This method has the characteristics that the time required for breeding can be efficiently reduced by analyzing the cross progeny by using a DNA marker when the progeny is a juvenile plant.

Also, the genomic selection is a technique in which a prediction formula is created from a phenotype obtained in advance and genome information, to predict the characteristics from the prediction formula and the genome information without any evaluation of the phenotype, and is a technology contributing to improvement in efficient breeding. The new breeding techniques are a generic term of variety improvement (=breeding) techniques that are combinations of molecular biological techniques. Examples of the new breeding techniques include cisgenesis/intragenesis, introduction of an oligonucleotide-directed mutation, RNA-dependent DNA methylation, genome editing, grafting onto a GM rootstock or scion, reverse breeding, agroinfiltration, and seed production technology (SPT). The genome editing technologies are those in which gene information is transformed in a sequence-specific manner which enables, for example, deletion of a base sequence, substitution of an amino sequence, and introduction of an exogenous gene. Examples of tools for these techniques include sequence-specific genome modification techniques such as zinc-finger nuclease (ZFN), TALEN, CRISPR/Cas9, CRISPER/Cpf1, and Meganuclease which each enable sequence-specific DNA scission and CAS9 Nickase and Target-AID which are each created by modifying the aforementioned tools.

Examples of the crops mentioned above include crops listed in GM APPROVAL DATABASE of genetically modified crops in the electronic information site (http://www.isaaa.org/) of INTERNATIONAL SERVICE for the ACQUISITION of AGRI-BIOTECH APPLICATIONS (ISAAA). More specifically, these examples include herbicide tolerant crops, harmful insect tolerant crops, disease resistant crops, and quality modified (for example, increase or decrease in content or change in composition) crops of products (for example, starch, amino acid, and fatty acid), fertile trait modified crops, abiotic stress tolerant crops, or crops modified in traits relating to growth and yield.

Examples of crops having tolerance to different herbicides are given as follows.

The mechanism of tolerance to herbicides is obtained, for example, by reducing the compatibility of a chemical with its target, by rapid metabolism (for example, breakdown or modification) resulting from the expression of a chemical deactivation enzyme, or by inhibiting the incorporation of a chemical into a plant body or the transfer of the chemical in the plant body.

The crops to which herbicide tolerance is imparted by genetic recombination technologies include crops to which tolerances to the following inhibitors are imparted by genetic recombination technologies: 4-hydroxyphenyl pyruvate dioxygenase (hereinafter abbreviated as HPPD) inhibitors such as isoxaflutole and mesotrione, acetolactate synthetase (hereinafter: abbreviated as ALS) inhibitors such as imidazolinone type herbicides containing imazethapyr and sulfonylurea type herbicides containing thifensulfuron-methyl, 5-enolpyruvylshikimate-3-phosphate synthase (hereinafter abbreviated as EPSP) inhibitors such as glyphosate, glutamine synthetase inhibitors such as glufosinate, auxin type herbicides such as 2,4-D and dicamba, and oxynil type herbicides containing bromoxynil. Examples of the herbicide tolerant crops are shown below:

Glyphosate herbicide tolerant crops: which are obtained by introducing one or more of a glyphosate tolerant EPSPS gene (CP4 epsps) derived from *Agrobacterium tumefaciens* strain CP4, glyphosate metabolism enzyme gene (gat4601, gat4621) obtained by strengthening the metabolism activity of a glyphosate metabolism enzyme (glyphosate N-acetyltransferase) gene derived from *Bacillus licheniformis* by shuffling technologies, glyphosate metabolism enzyme (glyphosate oxidase) gene (goxv247) derived from Ochrobacterum *anthropi* strain (LBAA), or EPSPS gene (mepsps, 2mepsps) having a glyphosate tolerance mutation derived from corn. Examples of main crops include rapeseed (*Brassica napus*), cotton (*Gossypium hirsutum* L.), corn (*Zea mays* L.), soybean (*Glycine max* L.), and sugar beet (*Beta vulgaris*). Some of these glyphosate tolerant transgenic crops are commercially available. For example, genetically modified crops expressing glyphosate tolerant EPSPS genes derived from *Agrobacterium* strains are commercially available under the names including "Roundup Ready (registered trademark)", genetically modified crops expressing a glyphosate metabolism enzyme which is derived from *Bacillus subtilis* and obtained by strengthening its metabolism activity by shuffling technologies are commercially available under the names of "Optimum (registered trademark) GAT (trademark)", "Optimum (registered trademark) Gly canola", and the like. Genetically modified crops expressing the EPSPS genes having a glyphosate tolerance mutation derived from corn are commercially available under the name of "GlyTol (trademark)".

Glufosinate herbicide tolerant crops: which are obtained by Introducing one or more of a phosphinothricin N-acetyltransferase (PAT) gene (bar) which is a glufosinate metabolism enzyme derived from *Streptomyces hygroscopicus*, phosphinothricin N-acetyltransferase (PAT) enzyme gene (pat) which is a glufosinate metabolism enzyme derived from Streptomyes *viridochromogenes*, and a synthesized pat gene (pat syn) derived from Streptomyes *viridochromogenes* strain Tu494. Examples of main crops include rapeseed (*Brassica napus*), cotton (*Gossypium hirsutum* L.), corn (*Zea mays* L.), soybean (*Glycine max* L.), and sugar beet (*Beta vulgaris*). Some of these glufosinate tolerant transgenic crops are commercially available. For example, genetically modified crops derived from a glufosinate metabolism enzyme (bar) derived from *Streptomyces hygroscopicus* and genetically modified crops derived from Streptomyes *viridochromogenes* are commercially available under the names including "LibertyLink (trademark)", "InVigor (trademark)", and "WideStrike (trademark)". Oxynil type herbicides (for example, bromoxynil" tolerant crops: there are oxynil type herbicides, for example, bromoxynil tolerant transgenic crops, which are obtained by introducing a nitrilase gene (bxn) which is an oxynil type herbicide (for example, bromoxynil) metabolism enzyme derived from *Klebsiella pneumoniae* subsp. Ozaenae). Examples of main crops include rapeseed (*Brassica napus*) and cotton (*Gossypium hirsutum* L.). These crops are commercially available under the names including "Navigator (trademark) canola" and "BXN (trademark)". There are also the following crops commercially available under the following names: ALS herbicide tolerant crops: Corn (*Zea mays* L.) "Optimum (trademark) GAT (trademark)" which is obtained by introducing an ALS herbicide tolerant ALS gene (zm-hra) derived from corn and is tolerant to sulfonylurea-type and imidazolinone-type herbicides; Soybean "Cultivance" which is obtained by introducing an ALS herbicide tolerant ALS gene (csr1-2) derived from thale cress and is tolerant to imidazolinone type herbicides; and Soybean "Treus (trademark)", "Plenish (trademark)", and "Optimum GAT (trademark)", which is obtained by introducing an ALS herbicide tolerant ALS gene (gm-hra) derived from soybean (*Glycine max*) and is tolerant to sulfonylurea type herbicides. Also, cotton is available into which an ALS herbicide tolerant ALS gene derived from tobacco (*Nicotiana tabacum* cv. Xanthi) is introduced. HPPD herbicide tolerant crops: soybean into which mesotrione tolerant HPPD genes (avh-ppd-03) derived from oats (*Avena sativa*) and phosphinothricin N-acetyltransferase (PAT) enzyme genes (pat) tolerant to mesotrione which is a glufosinate metabolism enzyme derived from Streptomyes *viridochromogenes* are both introduced is commercially available under the name of "Herbicide-tolerant Soybean line (trademark)".

2,4-D tolerant crops: corn obtained by introducing aryloxyalkanoate dioxygenase genes (aad-1) which are a 2,4-D metabolism enzyme derived from Sphingobium *herbicidovorans* is commercially available under the name of "Enlist (trademark) maize". There are soybean and cotton obtained by introducing an allyloxyalkanoate dioxygenase gene (aad-12) which is a 2,4-D metabolism enzyme derived from Delftia *acidovorans* and these crops are commercially available under the name of "Enlist (trademark) Soybean".

Dicamba tolerant crops: there are soybean and cotton obtained by introducing a Dicamba monooxygenase gene (dmo) which is a dicamba metabolism enzyme derived from *Stenotrophomonas maltophilia* strain DI-6. Soybean (*Glycine max* L.) obtained by introducing, in addition to the above gene, a glyphosate tolerant type EPSPS gene (CP4 epsps) derived from *Agrobacterium tumefaciens* strain CP4 is commercially available under the name of "tenuity (registered trademark) Roundup Ready (trademark) 2 Xtend (trademark)".

Examples of commercially available products of the transgenic crops to which herbicide tolerance is imparted include glyphosate tolerant corn: "Roundup Ready Corn", "Roundup Ready 2", "Agrisure GT", "Agrisure GT/CB/LL", "Agrisure GT/RW", "Agrisure 3000GT", YieldGard VT Rootworm/RR2", and "YieldGard VT Triple"; glyphosate resistant soybean: "Roundup Ready Soybean" and "Optimum GAT"; glyphosate tolerant cotton: "Roundup Ready Cotton" and "Roundup Ready Flex"; glyphosate tolerant rapeseed: "Roundup Ready Canola"; glufosinate tolerant corn: "Roundup Ready 2", "Liberty Link", "Herculex 1", "Herculex RW", "Herculex Xtra", "Agrisure GT/CB/LL", "Agrisure CB/LL/RW", and "Bt10"; glufosinate tolerant cotton: "FiberMax Liberty Link"; glufosinate tolerant rapeseed: "in Vigor"; bromoxynil tolerant cotton: "BXN"; bromoxynil tolerant rapeseed: "Navigator" and "Compass". Further crops modified in respect to herbicides are widely known. Examples of these crops include glyphosate tolerant crops such as rapeseed, sugar beet, and sunflower (see, for example, U.S. Pat. Nos. 5,188,642, 4,940, 835, 5,633,435, 5,804,425, and 5,627,061); dicamba tolerant crops such as cotton, soybean, pea, sunflower, and corn (see, for example, WO2008051633, U.S. Pat. Nos. 7,105,724, and 5,670,454); glufosinate tolerant crops such as soybean and sugar beet (see, for example, U.S. Pat. Nos. 6,376,754, 5,646,024, and 5,561,236); 2,4-D tolerant crops such as cotton, sunflower, corn, and soybean (see, for example, U.S. Pat. Nos. 6,153,401, 6,100,446, WO2005107437, U.S. Pat. Nos. 5,608,147, and 5,670,454); crops tolerant to acetolactate synthase (ALS) inhibitors (for example, sulfonylurea type herbicides and imidazolinone type herbicides) such as rapeseed, corn, cotton, rapeseed, soybean, and sunflower (see, for example, U.S. Pat. No. 5,013,659, WO2006060634, U.S. Pat. Nos. 4,761,373, 5,304,732, 6,211,438, 6,211,439, and 6,222,100); crops tolerant to PPO inhibitors having PPO reduced in compatibility with the inhibitors and/or having an ability which can detoxify or decompose these PPO inhibitors by the aid of cytochrome P450 monooxygenase (see, for example, WO2011085221, WO2012080975, WO2014030090, WO2015022640, WO2015022636, WO2015022639, WO2015092706, WO2016203377, WO2017198859, WO2018019860, WO2018022777, WO2017112589, WO2017087672, WO2017039969, WO2017023778, and Pest Management Science, 61, 2005, 277-285) such as corn, cotton soybean, and rapeseed; and crops tolerant to HPPD inhibitors (for example, isoxazole type herbicides such as isoxaflutole, triketone type herbicides such as sulcotrione and mesotrione, pyrazole type herbicides such as pyrazolynate, and diketonitrile which is a degradation product of isoxaflutole), such as corn, soybean, cotton, rape seed, and sugar beet (see, for example, WO2004/055191, WO199638567, WO1997049816 and U.S. Pat. No. 6,791,014).

Examples of crops to which herbicide tolerance is imparted classically or by genome breeding technologies include sunflower "Clearfield Sunflower" and rape seed "Clearfield canola" (BASF products), which are each tolerant to imidazolinone type ALS inhibitors such as imazethapyr and imazamox; soybean "STS soybean" tolerant to sulfonyl type ALS inhibitors such as thifensulfuron-methyl; sethoxydim tolerant corn "SR corn" and "Poast Protected (registered trademark) corn" having tolerance to acetyl CoA carboxylase inhibitors such as trione-oxime type or aryloxyphenoxypropionate type herbicides; sunflower "ExpressSun (registered trademark)" having tolerance to sulfonylurea type herbicides such as tribenuron-methyl; and rapeseed "Triazinon Tolerant Canola" having tolerance to a PSII inhibitor.

Examples of crops to which herbicide tolerance is imparted by genome editing technologies include rape seed "Su Canola (registered trademark)" having tolerance to sulfonylurea type herbicides and which are developed using Rapid Trait Development System (RTDS) (registered trademark). This RTDS (registered trademark) is a technology corresponding to the introduction of an oligonucleotide-directed mutation in genome editing technologies and is a technology enabling the introduction of a mutation through Gene Repair Oligonucleotide (GRON), that is, DNA-RNA chimeric oligonucleotide without cutting of DNA in the plant. Also, herbicide tolerant corn reduced in phytic acid content by using zinc finger nuclease to delete an endogenous gene IPK1 (see, for example, Nature 459, 437-441, 2009).

With regard to the crops to which herbicide tolerance is imparted, examples in which the nature of a rootstock is transferred to a scion in breeding technologies utilizing grafting include an example in which glyphosate tolerance is imparted to a scion of non-transgenetic soybean by using Roundup Ready (registered trademark) soybean having glyphosate tolerance as the rootstock (see, Weed Technology 27:412-416, 2013).

The crops in the present invention may be imparted with further traits that are different from herbicide tolerance, such as insect resistance, disease resistance, abiotic stress tolerance, enhanced nutrient contents and utilization, fertility/sterility modification, harvest quality improvements, and growth/yield improvements, and so on.

Examples of crops to which pest resistance is imparted are shown below.

Examples of crops to which resistance to lepidopterous pests is imparted by genetic recombination technologies include crops such as corn (*Zea mays* L.), soybean (*Glycine max* L.), and cotton (*Gossypium hirsutum* L.) each obtained by introducing a gene encoding δ-endotoxin which is an insecticidal protein derived from *Bacillus thuringiensis*

(hereinafter abbreviated as Bt bacteria) which is soil bacteria. Examples of the δ-endotoxin imparting resistance to lepidopterous pests include Cry1A, Cry1Ab, modified Cry1Ab (partially deficient Cry1Ab), Cry1Ac, Cry1Ab-Ac (hybrid protein of combined Cry1Ab and Cry1Ac), Cry1C, Cry1F, Cry1Fa2 (modified crylF), moCry1F (modified Cry1F), Cry1A.105 (hybrid protein of combined Cry1Ab, Cry1Ac, and Cry1F), Cry2Ab2, Cry2Ae, Cry9C, Vip3A, and Vip3Aa20. Examples of crops to which resistance to coleopterous pests is imparted by genetic recombination technologies include crops such as corn, each obtained by introducing a gene encoding δ-endotoxin which is an insecticidal protein derived from Bt bacteria which are soil bacteria. Examples of the δ-endotoxin imparting resistance to coleopterous pests include Cry3A, mCry3A (modified Cry3A), Cry3Bb1, Cry34Ab1, and Cry35Ab1. Examples of crops to which resistance to dipterous pests is imparted by genetic recombination technologies include crops such as genetically modified corn (*Zea mays* L.) obtained by introducing a synthesized gene encoding a hybrid protein eCry3.1Ab of a combination of Cry3A and Cry1Ab derived from Bt bacteria which are soil bacteria, and genetically modified cotton (*Gossypium hirsutum* L.) obtained by introducing a gene encoding a trypsin inhibitor CpTI derived from cowpea (*Vigna* unguiculate). Further examples include genetically modified poplar obtained by introducing a gene encoding API which is a protease inhibitor protein A derived from arrowhead (*Sagittaria sagittifolia*). These crops have tolerance to a wide range of pests.

The insecticidal proteins imparting pest resistance to crops include hybrid proteins of the above insecticidal proteins, partially deficient proteins, and modified proteins. The hybrid proteins are produced by a combination of different domains of a plurality of insecticidal proteins and for example, Cry1Ab-Ac and Cry1A.105 are known. As the partially deficient proteins, Cry1Ab deficient in a part of amino acid sequences is known. As the modified proteins, Cry1Fa2, moCry1F, mCry3A, and the like are known that are proteins in which one or plural amino acids of natural type δ-endotoxin are substituted. Also, in the amino acid substitution like this, a protease recognition sequence which does not exist in nature is preferably inserted into toxin as shown in the case (see WO2003/018810) of Cry3A055.

Monsanto Company has developed cotton (evento MON88702) obtained by introducing a modified BT protein Cry51Aa2 (Cry51Aa2.834 16) by genetic recombination technologies and the cotton has resistance to genus *lygus* such as *Lygus lineolaris*, Hemiptera such as aphid and Thysanoptera such as genus *Frankliniella*.

Other than the above, examples of the insecticidal protein imparting pest resistance to crops by genetic recombination technologies include insecticidal proteins derived from *Bacillus cereus* or *Bacillus popilliae*, vegetable proteins Vip1, Vip2, Vip3, and Vip3A derived from Bt bacterium strain AB88, insecticidal proteins derived from nematode symbiotic (forms a colony in nematode) bacteria, for example, *Photorhabdus* spp. such as *Photorhabdus luminescens* and Xenorhabdus *nematophilus* and Xenorhabdus spp. such as Xenorhabdus *nematophilus*, toxins produced from animals having neurotoxins specific to insects, such as a scorpion toxin, spider toxin, and bee toxin, toxins of filamentous fungi such as a Streptomycetes toxin, vegetable lectin such as pea lectin, barley lectin, and snowdrop lectin, protease inhibitors such as agglutinin, trypsin inhibitor, serine protease inhibitor, protease inhibitors such as patatin, cystatin, and papain inhibitor, ribosome inactivation proteins (RIP) such as lysine, corn-RIP, abrin, luffin, saporin, and bryodin, steroid metabolism enzymes such as 3-hydroxysteroidoxydase, ecdysteroid-UDP-glucosyltransferase, and cholesterol oxidase, ion channel inhibitors such as an ecdysone inhibitor, HMG-CoA-reductase, and sodium channel or calcium channel inhibitor, juvenile hormone esterase, diuretic hormone receptor, stilbene synthase, bibenzyl synthase, chitinase, and glucanase.

Crops to which pest resistance is imparted by introducing one or two or more insecticidal protein genes have been already known and some of these crops are commercially available. Examples of cotton having pest resistance include "Bollgard (trademark) cotton", "BXN (trademark) Plus Bollgard (trademark) Cotton", "BXN (trademark) Plus Bollgard (trademark) Cotton", "JK 1", "Roundup Ready (trademark) Bollgard (trademark) Cotton", and "Ingard (trademark)", which each express an insecticidal protein Cry1Ac derived from Bt bacteria, "Herculex(trademark) I" and "Herculex(trademark) CB", which each express an insecticidal protein modified Cry1F (Cry1Fa2) derived from Bt bacteria; "VIPCOT (trademark) Cotton" expressing an insecticidal protein Vip3A derived from Bt bacteria; "Bollgard II (trademark) cotton", "Roundup Ready(trademark) Bollgard II (trademark) Cotton", "Roundup Ready (trademark) Flex (trademark) Bollgard II (trademark) Cotton" and "Fivermax (trademark) Liberty Link (trademark) Bollgard II (trademark)", which each express insecticidal proteins Cry1Ac and Cry2Ab derived from Bt bacteria; "Bollgard III (registered trademark) cotton" and "Bollgard (registered trademark) III×Roundup Ready (trademark) Flex (trademark)", which express insecticidal proteins Cry1Ac, Cry2Ab, and Vip3A derived from Bt bacteria, "VIPCOT (trademark) Roundup Ready Flex (trademark) Cotton" expressing insecticidal proteins Vip3A and Cry1Ab derived from Bt bacteria; "VIPCOT (registered trademark)" expressing insecticidal proteins Vip3A and Cry1Ac derived from Bt bacteria; "WideStrike (trademark) Cotton", "WideStrike (trademark) Roundup Ready (trademark) Cotton", and "Widestrike (trademark) Roundup Ready Flex (trademark) Cotton", which express insecticidal proteins Cry1Ac and Cry1F derived from Bt bacteria; "VIPCOT (trademark) Cotton expressing an insecticidal protein Vip3A derived from Bt bacteria; "Twinlink (trademark) Cotton" and "Glytol (trademark)×Twinlink (trademark), which express insecticidal proteins Cry1Ab and Cry2Ae derived from Bt bacteria; "Widestrike (registered trademark) 3" and "Widestrike (trademark)×Roundup Ready Flex (trademark)×VIPCOT (trademark) Cotton", which express insecticidal proteins Cry1Ac, Cry1F, and Vip3A derived from Bt bacteria; and "Glytol (trademark)×Twinlink (trademark)×VIPCOT (trademark) Cotton" expressing insecticidal proteins Cry1Ab, Cry2Ae, and Vip3A derived from Bt bacteria.

Examples of the corn having pest resistance include "YieldGard (registered trademark) Rootworm RW", "YieldGard (trademark) RW+RR", "YieldGard (trademark) VT (trademark) Rootworm (trademark) RR2", and "MaxGard (trademark)", which express an insecticidal protein Cry3Bb1 derived from Bt bacteria; "YieldGard (registered trademark) VT Triple" and "YieldGard (trademark) Plus with RR", which express insecticidal proteins Cry3Bb1 and Cry1Ab derived from Bt bacteria; "Bt Xtra (trademark) Maize" expressing an insecticidal protein Cry1Ac derived from Bt bacteria; "YieldGard Plus (registered trademark)" expressing insecticidal proteins Cry1Ab and Cry3Bb1 derived from Bt bacteria; "Bt10", "Liberty Link(trademark) Yieldgard (trademark) Maize", "Agrisure (trademark) GT/CB/LL", and "YieldGard (trademark) CB+RR" expressing an insecticidal protein Cry1Ab derived from Bt bacteria;

"YieldGard (trademark) VT Pro (trademark)" and "tenuity (registered trademark) VT Double Pro (trademark)", which express insecticidal proteins Cry1A. 105 and Cry2Ab2 derived from Bt bacteria; "Agrisure (registered trademark) RW" and "Agrisure (trademark) GT/RW", which express an insecticidal protein mCry3A derived from Bt bacteria; "Starlink (trademark) Maize" expressing an insecticidal protein Cry9C derived from Bt bacteria; "YieldGard (trademark)", "MaizeGard (trademark)", "NaturGard KnockOut (trademark)", "Maximizer (trademark)", "Roundup Ready (trademark) YieldGard (trademark) Maize", "Agrisure (trademark) CB/LL", and "Mavera (trademark) YieldGard (trademark) Maize", which express an insecticidal protein Cry1Ab derived from Bt bacteria; "Agrisure (registered trademark) 3122" expressing insecticidal proteins Cry1Ab, Cry1F, modified Cry3A, Cyr34Ab1, and Cyr35Ab1 derived from Bt bacteria; "Agrisure (registered trademark) Viptera" expressing an insecticidal protein Vip3Aa20 derived from Bt bacteria; "Agrisure (registered trademark) Viptera (trademark) 2100" and "Agrisure (registered trademark) Viptera (trademark) 3110", which express insecticidal proteins Vip3Aa20 and Cry1Ab derived from Bt bacterial; "Agrisure (registered trademark) Viptera (trademark) 3100", "Agrisure (registered trademark) Viptera (trademark) 3111" and "Agrisure (registered trademark) Viptera (trademark) 4", which express insecticidal proteins Vip3Aa20, Cry1Ab, and modified Cry3A derived from Bt bacteria; "Agrisure (registered trademark) Viptera (trademark) 3220" expressing insecticidal proteins Vip3Aa20, Cry1Ab, and modified Cry1F derived from Bt bacteria; "Agrisure (registered trademark" Duracade (trademark)" expressing an insecticidal protein eCry3.1Ab (Cry3A-Cry1Ab chimera protein) derived from Bt bacteria; "Agrisure (registered trademark) Duracade (trademark) 5122" expressing insecticidal proteins eCry3.1Ab (Cry3A-Cry1Ab chimera protein), modified Cry3A, Cry1Ab, and modified Cry1F derived from Bt bacteria; "Agrisure (registered trademark) Duracade (trademark) 5222" expressing insecticidal proteins eCry3.1Ab (Cry3A-Cry1Ab chimera protein), modified Cry3A, modified Cry1Ab, and Vip3A variant derived from Bt bacteria; "Herculex (trademark) RW" expressing insecticidal proteins Cyr34Ab1 and Cyr35Ab1 derived from Bt bacteria; "Herculex XTRA (trademark)" expressing insecticidal proteins Cyr34Ab1, Cyr35Ab1, and Cry1F derived from Bt bacteria; "Genuity (registered trademark) VT Triple Pro (trademark)" expressing insecticidal proteins Cry1A. 105, Cry2Ab2, and Cry3Bb1 derived from Bt bacteria; "Genuity (registered trademark) SmartStax (trademark)" expressing insecticidal proteins Cry1F, Cry2Ab, Cyr34Ab1, Cyr35Ab1, Cry3Bb1, and Cry1A. 105 derived from Bt bacteria; "Power Core (trademark)" expressing insecticidal proteins, modified Cry1F, Cry2Ab, and Cry1A. 105 derived from Bt bacteria; "Herculex XTRA (trademark) RR" expressing insecticidal proteins Cry1F, Cyr34Ab1, and Cyr35Ab1 derived from Bt bacteria; "Optimum (registered trademark) Intrasect Xtreme" expressing insecticidal proteins, modified Cry1F, Cyr34Ab1, Cyr35Ab1, Cry1Ab, and modified Cry3A derived from Bt bacteria; "Optimum (registered trademark) Intrasect XTRA" expressing insecticidal proteins, modified Cry1F, Cyr34Ab1, Cyr35Ab1, and Cry1Ab derived from Bt bacteria; and "Optimum (registered trademark) TRIsect" expressing insecticidal proteins, modified Cry1F and modified Cyr3A derived from Bt bacteria: these products being all commercially available.

Examples of other crops having pest resistance include soybean "Intacta (trademark) Roundup Ready (trademark) 2 Pro" expressing an insecticidal protein Cry1Ac derived from Bt bacteria, these products being each commercially available.

Specifically, the following crop products are available: corn "YieldGard corn rootworm" and "YieldGard VT", "Herculex RW" and "Herculex Rootworm", and "Agrisure CRW", which have resistance to corn rootworms; corn "YieldGard corn borer", "YieldGard plus" and "YieldGard VT Pro", "Agrisure CB/LL" and "Agrisure 3000GT", "Hercules I", and "Hercules II", "KnockOut", "NatureGard", and "StarLink", which have resistance to corn borers; corn "Herculex I" and "Herculex Xtra", "NewLeaf", "NewLeaf Y", and "NewLeaf Plus", which have resistance to western bean cutworms, corn borers, black cutworms, and fall armyworms; corn "YieldGard Plus" having resistance to corn borers and corn rootworms; cotton "Bollgard I" and "Bollgard II", which have resistance to *Heliothis virescens*; and cotton "Bollgard II", "WideStrike", and "VipCot", which have resistance to *Heliothis virescens*, cotton bollworms, fall armyworms, beet armyworms, cabbage loopers, soybean loopers, and pink bollworms.

As crops to which insect pest resistance is imparted by RNA interference technologies, corn resistant to Lepidoptera insect pests (for example, corn borers, cutworms such as corn earworms and black cutworms, and fall armyworms) and Coleoptera insect pests (corn rootworms) is commercially available or is developed under the names of "SmartStax (registered trademark)", "SmartStax (registered trademark) Pro", "Genuity (registered trademark) SmartStax".

Examples of crops to which pest resistance is imparted classically or by genome breeding technologies include aphid resistant soybean having a Rag1 (Resistance Aphid Gene 1) gene; soybean having resistance to Cysto nematode; cotton having resistance to Root Knot nematode; and soybean "FUKUNOMINORI" having resistance to *Spodoptera litura*.

Resistance to optional insect pests (especially Lepidoptera insects, Coleoptera insects, and Diptera insects), noxious arachnids, and noxious nematodes are imparted to crops to which resistance to these insect pests is imparted. Crops to which pest resistance is imparted are preferably selected from corn, rape seed, soybean, sugar beet, and sunflower, more preferably selected from soybean, corn, and cotton.

Examples of the crops to which disease resistance is imparted are given below.

Crops to which disease resistance is imparted by genetic recombination technologies are those expressing so-called "pathogen related proteins" (PRP, see, for example, EP0392225) or so-called "antifungal proteins" (AFP, see, for example, U.S. Pat. No. 6,864,068). Various antifungal proteins having activity to plant pathogenic fungi are isolated from specific crops and become commonly used. Examples of such pathogenic substances and crops enabling synthesis of these plant pathogenic substances are well known from EP0392225, WO1993/05153, WO1995/33818, and EP0353191. Crops resistant to fungicidal pathogens, viral pathogens, and bacterial pathogens are produced by introducing plant disease resistant genes.

Examples of crops in which contents in these crops are modified are given below.

The modification of contents in a plant implies increase and decrease in synthesis of modified compounds or synthetic amount of chemical substances as compared with the corresponding wild-type crops. There are, for example, modified crops increased or decreased in the contents of vitamins, amino acids, proteins, and starch, and various oils and modified crops reduced in nicotine content.

Examples of crops modified in content by genetic recombination technologies include rape seed "Laurical (trademark) Canola" increased in the content of triacylglyceride containing lauric acid by introducing 12: 0 ACP thioesterase derived from laurier (*Umbellularia californica*) relating to fatty acid synthesis; soybean "Plenish (trademark)" or "Treus (trademark)" increased in oleic acid content through reduction of gene expression by introducing a partial gene sequence (gm-fad2-1) of ω-6 desaturase which is an unsaturated enzyme of fatty acid and is derived from soybean; Soybean "Vistive Gold (trademark)" reduced in fatty acid content by introducing a gene creating a double strand DNA of an acyl-acyl carrier-protein-thioesterase gene (fatb1-A) derived from soybean and a gene creating a double strand DNA of a 6-12 desaturase gene (fad2-1A) derived from soybean; genetically modified soybean increased in the content of ω3 fatty acid by introducing a 6-6 desaturase gene (Pj.D6D) derived from primrose and 6-12 desaturase gene (Nc. Fad3) derived from red bread mold; corn "Enogen (registered trademark)" increased in productivity of bioethanol by introducing a heat resistant α-amylase gene (amy797E) of Thermococcales sp. relating to amylolysis; corn "Mavera (trademark) Maize" and "Mavera (trademark) YieldGard (trademark) Maize" increased in productivity of lysin by introducing a dihydrodipicolinate synthetase gene (cordapA) derived from *Corynebacterium glutamicum* relating to the production of lysin that is an amino acid.

As crops modified in content either classically or by genome breeding technologies, rape seed "Nexera (registered trademark) Canola" producing unsaturated ω-9 fatty acid; and soybean "Yumeminori" reduced in allergen content.

Crops modified in plant nutrient utilization are those improved in assimilation or metabolization of nitrogen or phosphorus. Crops having nitrogen assimilation ability and nitrogen utilization ability enhanced by genetic recombination technologies are selected from rape seed, corn, sunflower, soybean, cotton, and sugar beet (see, for example, WO1995009911, WO1997030163, U.S. Pat. Nos. 6,084, 153, 5,955,651, and 6,864,405). Crops improved in phosphorous uptake by genetic recombination technologies include rape seed, corn, cotton, soybean, sugar beet, and sunflower (see, for example, U.S. Pat. No. 7,417,181 and US 20050137386). The methods of manufacturing such crops are generally known to a person skilled in the art and these crops are, for example, disclosed in the above publications.

As crops modified in fertility trait and the like by genetic recombination technologies, crops to which male sterility and fertility restoring traits are imparted are exemplified. Examples of these crops include corn to which a male sterility trait is imparted by expressing a ribonuclease gene (barnase) derived from *Bacillus amyloliquefaciens* in tapetum cells of an anther; corn to which male sterility trait is imparted by introducing a DNA adeninemethylase gene (dam) derived from *Escherichia coli*; corn controlled in fertility trait by introducing an α-amylase gene (zm-aal) derived from corn imparting a male sterility trait and a ms45 protein gene (ms45) derived from corn imparting a fertility restoring trait; rape seed to which fertility restoring ability is imparted by expressing a ribonuclease inhibitory protein gene (barstar) derived from *Bacillus* in tapetum cells of an anther; and rape seed controlled in a fertility trait by expressing a ribonuclease gene (barnase) derived from *Bacillus* imparting a male sterility trait and a ribonuclease inhibitory protein gene (barstar) derived from *Bacillus* imparting a fertility restoring trait. Other examples of crops to which a fertility trait is imparted by genetic recombination technologies include soybean and sunflower (see, for example, U.S. Pat. Nos. 6,720,481, 6,281,348, 5,659,124, 6,399,856, 7,345,222, 7,230,168, 6,072,102, EP1135982, WO2001092544, and WO1996040949). The methods of manufacturing such crops are generally known to a person skilled in the art and these crops are, for example, disclosed in the above publications. These crops are preferably selected from corn, rape seed, and soybean.

Crops to which abiotic stress tolerance is imparted are those increased in tolerance to abiotic stress condition such as drought, high salt content, high light intensity, high UV irradiation, chemical contamination (for example, high concentrations of heavy metals), low or high temperature, limited supply of nutrients, and collective stress (see, for example, WO200004173, WO2007131699, CA2521729, and US20080229448).

Examples of crops to which abiotic stress tolerance is imparted include corn, soybean, rape seed, and cotton, which have tolerance to drought (see, for example, WO2005048693, WO2008002480, and WO 2007030001); corn, soybean, cotton, and rape seed, which have tolerance to low temperature (see, for example, U.S. Pat. No. 4,731, 499 and WO2007112122); and cotton, soybean, and sunflower, which have tolerance to high salt content (see, for example, U.S. Pat. Nos. 7,256,326, 7,034,139, and WO/2001/030990). Examples of these crops also include corn "DroughtGard (registered trademark)" (product from Monsanto) into which a cold shock protein gene cspB of *Bacillus subtilis* is introduced.

As the crops to which abiotic stress tolerance is imparted either classically or by genome breeding technologies, for example, corn having drought tolerance are commercially available under the names of "Agrisure Artesian (registered trademark) and "Optimum (registered trademark) AQUAmax (trademark)".

Examples of crops modified in other qualities by genetic recombination technologies include rape seed "Phytaseed (registered trademark) Canola" improved in the degradation of endogenous phytic acid by introducing a 3-phytase gene (phyA) derived from *Aspergillus niger* that is an enzyme that breaks down plant phytic acid; and cotton producing high-quality fibers improved in fiber micronaire, fiber strength increase, length uniformity, and color (see, for example, WO 1996/26639, U.S. Pat. Nos. 7,329,802, 6,472,588, and WO 2001/17333).

Examples of crops modified in plant growth and yield include crops improved in growing ability. As crops modified by genetic recombination technologies, soybean has been developed which is improved in plant growth with the expectation of resultant high yield by introducing a gene (bbx32) encoding a transcription factor controlling daily periodicity specific to thale cress; and corn has been also developed which is increased in female panicle weight with the expectation of resultant high yield by introducing a transcription factor gene (athb17) belonging to homeodomain-leucine 14 zipper (HD-Zip) family, class II (HD-Zip II) derived from thale cress.

Examples of crops modified in quality by genome editing technologies include corn "ZFN-12 maize" reduced in phytic acid content by using zinc finger nuclease to delete an IPK1 gene encoding inositol-1,3,4,5,6-pentakisphosphate 2-kinase that is a phytic acid synthetic enzyme; and mushroom to which browning tolerance is imparted by using CRISPR-Cas9 to delete a gene encoding a polyphenol oxidase (see, for example, Nature., Vol 532, 21 APRIL, 2016).

The above crops include plant lines added with two or more of the properties like those mentioned above, for example, abiotic stress tolerance, disease resistance, herbicide tolerance, pest tolerance, growth and yield traits, nutrient-uptake, product qualities, and sterility trait by using genetic recombination technologies, classical breeding technologies, genome breeding technologies, new breeding technologies, or genome editing technologies and plant lines added with two or more of natures specific to parent lines by crossing lines with a plant of the same kind, or with a plant having different natures.

Examples of commercially available crops to which tolerance to two or more herbicides is imparted include cotton "GlyTol (trademark) LibertyLink (trademark)" and "GlyTol (trademark) LibertyLink (trademark)" having tolerance to glyphosate and glufosinate; corn "Roundup Ready (trademark) LibertyLink (trademark) Maize" having tolerance to glyphosate and glufosinate; soybean "Enlist (trademark) Soybean" having tolerance to glufosinate and 2,4-D; soybean "tenuity (trademark) Roundup Ready (trademark) 2 Xtend (trademark)" having tolerance to glyphosate and dicamba; corn and soybean "OptimumGAT (trademark)" having tolerance to glyphosate and ALS inhibitors; genetically modified soybean "Enlist E3 (trademark)" and "Enlist (trademark) Roundup Ready 2 Yield (trademark)" having tolerance to three herbicides: glyphosate, glufosinate, and 2,4-D; genetically modified corn "Enlist (trademark) Roundup Ready (registered trademark) Corn 2" having tolerance to glyphosate, 2,4-D, and allyloxyphenoxypropionate type (FOPS) herbicides; genetically modified corn "Enlist (trademark) Roundup Ready (registered trademark) Corn 2" having tolerance to glyphosate, 2,4-D, and allyloxyphenoxypropionate type (FOPS) herbicides; genetically modified cotton "Bollgard II (registered trademark) XtendFlex (trademark) Cotton" having tolerance to dicamba, glyphosate, and glufosinate; and genetically modified cotton "Enlist (trademark) Cotton" having tolerance to three herbicides: glyphosate, glufosinate, and 2,4-D. Other than the above, cotton having tolerance to glufosinate and 2,4-D, cotton having tolerance to both glufosinate and dicamba, corn having tolerance to both glyphosate and 2,4-D, soybean having tolerance to both glyphosate and HPPD herbicides, and genetically modified corn having tolerance to glyphosate, glufosinate, 2,4-D, allyloxyphenoxypropionate type (FOPS) herbicides, and cyclohexadione type (DIMs) herbicides are also developed.

Examples of commercially available products of crops to which herbicide tolerance and pest resistance are imparted include corn "YieldGard Roundup Ready" and "YieldGard Roundup Ready 2" having glyphosate tolerance and corn borer resistance; corn "Agrisure CB/LL" having glufosinate tolerance and corn borer resistance; corn "Yield Gard VT Root worm/RR2" having glyphosate tolerance and corn rootworm resistance; corn "Yield Gard VT Triple" having glyphosate tolerance and corn rootworm resistance and corn borer resistance; corn "Herculex I" having glufosinate tolerance and Lepidoptera insect pest resistance (Cry1F) (resistance to, for example, a western bean cutworm, corn borer, black cutworm, and fall armyworm); corn "YieldGard Corn Rootworm/Roundup Ready 2" having glyphosate tolerance and corn root worm resistance; corn "Agrisure GT/RW" having glufosinate tolerance and Coleoptera insect pest resistance (Cry3A) (resistance to, for example, a western corn rootworm, northern corn rootworm, and Mexican corn rootworm); corn "Herculex RW" having glufosinate tolerance and Coleoptera insect pest resistance (Cry34/35Ab1) (resistance to, for example, a western corn rootworm, northern corn rootworm, and Mexican corn rootworm); corn "Yield Gard VT Root worm/RR2" having glyphosate tolerance and corn rootworm resistance; and cotton "Bollgard 3 (registered trademark) XtendFlex (registered trademark)" having dicamba tolerance, glyphosate tolerance, glufosinate tolerance, and Lepidoptera insect pest resistance (resistance to, for example, bollworms, tobacco budworm, and armyworms).

Examples of commercially available crops to which herbicide tolerance and modified product quality are imparted include rape seed "InVigor (trademark) Canola" to which glufosinate tolerance and fertility trait are imparted; corn "InVigor (trademark) Maize" to which glufosinate tolerance and fertility trait are imparted; and soybean "Vistive Gold (trademark)" modified in glyphosate tolerance and oil content.

Examples of commercially available crops having three or more traits include corn "Herculex I/Roundup Ready 2" having glyphosate tolerance, glufosinate tolerance, and Lepidoptera insect pest resistance (Cry1F) (specifically, resistance to western bean cutworm, corn borer, black cutworm, and fall armyworm); corn "YieldGard Plus/Roundup Ready 2" having glyphosate tolerance, corn rootworm resistance, and corn borer resistance; corn "Agrisure GT/CB/LL" having glyphosate tolerance, glufosinate tolerance, and corn borer resistance; corn "Herculex Xtra" having glufosinate tolerance, Lepidoptera insect pest resistance (Cry1F), and Coleoptera insect pest resistance (Cry34/35Ab1) (specifically, resistance to Lepidoptera insect pests such as a western bean cutworm, corn borer, black cutworm, and fall armyworm and resistance to Coleoptera insect pests such as western corn rootworm, northern corn rootworm, and Mexican corn rootworm); corn "Agrisure CB/LL/RW" having glufosinate tolerance, corn borer resistance (Cry1Ab), and Coleoptera insect pest resistance (Cry3A) (specifically, resistance to Coleoptera insect pests such as western corn rootworm, northern corn rootworm, and Mexican corn rootworm); corn "Agrisure (trademark) 3000GT" having glyphosate tolerance+corn borer resistance (Cry1Ab), and Coleoptera insect pest resistance (Cry3A) (specifically, resistance to western corn rootworm, northern corn rootworm, and Mexican corn rootworm); corn "Mavera high-value corn" having glyphosate tolerance, resistance to a corn rootworm and European corn borer, and a high lysine trait; corn "Optimum (registered trademark) Leptra (trademark)" having resistance to pests such as a European corn borer, southwestern corn borer, corn earworm, fall armyworm, black cutworm, and western beanworm causing damages on the ground, Soybean "Credenz (registered trademark) soybean" which is added with resistance to frogeye leaf spot, Sudden death syndrome, southern stem canker, *Phytophthora* root rot, southern root-knot nematode, *Sclerotinia* white mold, brown stem rot, and soybean cyst nematode, is improved in iron chlorosis, and is modified in chloride sensitivity, and cotton "Stoneville (registered trademark) Cotton" to which tolerance to a plurality of herbicides and pest resistance are imparted, while there are nine cotton varieties ST5517GLTP, ST4848GLT, ST4949GLT, ST5020GLT, ST5115GLT, ST6182GLT, ST4747GLB2, ST4946GLB2, and ST6448GLB2 to cope with the situation of the outbreak of weeds and noxious insects on the fields in various districts.

In the present method, the present composition or the present compounds (separately or jointly) is/are applied to the weeds or a soil of the place where the weeds are growing or will grow. The means for application include, for example, a process for spraying the soil with the present composition or the present compounds, and a process for spraying the weeds with the present composition or the present compounds.

The application rate of glufosinate or its salt in the present method is usually 100 to 2,000 g per 10,000 m², preferably 200 to 1,000 g per 10,000 m², more preferably 300 to 800 g per 10,000 m², and most preferably 655 g per 10,000 m² when expressed as glufosinate-ammonium equivalence (32 fluid ounces/acre of Liberty 280SL herbicide).

In the present method, an adjuvant may be mixed with the present composition or the present compounds to apply.

Although a type of the adjuvant is not particularly limited, the adjuvants include oils such as Agri-Dex and MSO, nonions (ester or ether of polyoxyethylene) such as Induce, anions (substituted sulfonate) such as Gramin S, cations (polyoxyethylene amine) such as Genamin T 200BM, and organic sillicons such as Silwett L77.

Although a pH and water hardness of the spray liquid prepared in the application of the present composition or the present compounds are not particularly limited, the pH is usually within a range of 5 to 9 and the water hardness is usually within a range of 0 to 500.

Although a period of time for doing the present method is not particularly limited, the period of time is usually within a range from 5 a.m. to 9 p.m., and the photon flux density at cultivation area when applying the present composition or the present compounds is usually 10 to 2500 µmol/m²/s. The spray pressure in the present method is usually 30 to 120 PSI and preferably 40 to 80 PSI though no particular limitation is imposed on it. Here, the spray pressure is a set value just before the dilution is introduced into the nozzle.

The nozzle used in the present method may be drift-reducing nozzles or standard nozzles. Examples of standard nozzles excluding drift-reducing nozzles include a Teejet110 series and XR Teejet110 series manufactured by Teejet Company. These nozzles are each operated under usual spray pressure (generally 30 to 120 PSI) and the volume median diameter of liquid droplets discharged from the nozzle is usually less than 430 micro meter. Examples of the drift-reducing nozzle to be used in the present method is a nozzle which is more reduced in drift as compared with a standard nozzle and which is called an air induction nozzle or pre-orifice nozzle. The volume median diameter of a liquid droplet discharged from the drift-reducing nozzle is usually 430 micro meter or more.

The air induction nozzle is a nozzle which is provided with an air introduction portion between the inlet (chemical dilution introduction portion) and outlet (chemical dilution discharge portion) of the nozzle to mix air with the chemical dilution thereby forming air-enriched liquid droplets. Examples of the air induction nozzle include TDXL11003-D, TDXL11004-D1, TDXL11005-D1, and TDXL11006-D manufactured by Green Leaf Technology Company, TTI110025, TTI11003, TTI11004, TTI11005, TTI110061, and TTI110081 manufactured by Teejet Company, and ULD120-041, ULD120-051, and ULD120-061 manufactured by Pentair Company. TTI11004 is particularly desirable.

The pre-orifice nozzle is a nozzle in which its inlet port (chemical dilution introduction portion) serves as a metering orifice which limits the amount of the fluid entering the inside of the nozzle to drop the pressure inside of the nozzle, thereby forming large droplets. The discharge pressure is thereby reduced by about half as compared with before the dilution is introduced into the nozzle. Examples of the pre-orifice nozzle include DR110-10, UR110-05, UR110-06, UR110-08, and UR110-10 manufactured by Wilger Company and 1/4TTJ08 Turf Jet and 1/4TTJ04 Turf Jet manufactured by Teejet Company.

The discharge pattern is preferably, though not particularly limited to, a flat fan type. As an example of the pattern excluding the flat fan type, a cone type is given.

When the present composition or the present compounds is/are applied to a row crop field, the present composition or the present compounds may be applied to the row crop field before seeding row crop seeds and the present composition or the present compounds may be applied concurrently with and/or after seeding row crop seeds. Namely, the present composition or the present compounds is/are applied once before, concurrently with, or after seeding row crop seeds; twice except before seeding row crop seeds, twice except concurrently with seeding row crop seeds, or twice except after seeding row crop seeds; or three times before, concurrently with, and after seeding row crop seeds.

When the present composition or the present compounds is/are applied before seeding row crop seeds, the present composition or the present compounds is/are applied from 50 days before seeding to immediately before seeding, preferably from 30 days before seeding to immediately before seeding, more preferably from 20 days before seeding to immediately before seeding, still preferably from 10 days before seeding to immediately before seeding.

When the present composition or the present compounds is/are applied after seeding row crop seeds, the present composition or the present compounds is/are applied normally from immediately after seeding to before flowering. The present composition or the present compounds is/are applied more preferably from immediately after seeding to before sprouting, or from 1 to 6 leaf stages of crops.

The case where the present composition or the present compounds is applied concurrently with seeding the row crop seeds is a case where a sowing machine and a spraying machine are integrated with each other.

Examples of the weeds which can be controlled by the present composition and the present method include the following weeds, but are not limited thereto.

Urticaceae weeds: *Urtica urens*

Polygonaceae weeds: *Polygonum convolvulus, Polygonum lapathifolium, Polygonum pensylvanicum, Polygonum persicaria, Polygonum longisetum, Polygonum aviculare, Polygonum arenastrum, Polygonum cuspidatum, Rumex japonicus, Rumex crispus, Rumex obtusifolius, Rumex acetosa*

Portulacaceae weeds: *Portulaca oleracea*, Trianthema portulacastrum

Caryophyllaceae weeds: *Stellaria media, Cerastium holosteoides, Cerastium glomeratum, Spergula arvensis, Silene gallica*

Molluginaceae weeds: *Mollugo verticillata* Chenopodiaceae weeds: *Chenopodium album, Chenopodium ambrosioides, Kochia scoparia, Salsola kali, Atriplex* spp.

Amaranthaceae weeds: *Amaranthus retroflexus, Amaranthus viridis, Amaranthus lividus, Amaranthus spinosus, Amaranthus hybridus, Amaranthus palmeri, Amaranthus rudis (Amaranthus tuberculatus=Amaranthus* tamariscinus), *Amaranthus patulus, Amaranthus blitoides, Amaranthus deflexus, Amaranthus quitensis, Alternanthera philoxeroides, Alternanthera sessilis, Alternanthera tenella*

Papaveraceae weeds: *Papaver rhoeas, Argemone mexicana* Brassicaceae weeds: *Raphanus raphanistrum, Raphanus sativus, Sinapis arvensis, Sinapis alba, Capsella bursa-pastoris, Brassica juncea, Brassica nigra, Descurainia pinnata, Rorippa islandica, Rorippa sylvestris, Thlaspi*

*arvense, Myagrum rugosum, Lepidium virginicum, Coronopus didymus, Descurainia sophia.*

Capparaceae weeds: Cleome *affinis* Fabaceae weeds: Aeschynomene indica, Aeschynomene *rudis, Sesbania exaltata, Cassia obtusifolia, Cassia occidentalis, Desmodium tortuosum, Desmodium adscendens, Trifolium repens, Pueraria lobata, Vicia angustifolia, Indigofera hirsuta, Indigofera truxillensis, Vigna sinensis*

Oxalidaceae: *Oxalis corniculata, Oxalis stricta, Oxalis* oxyptera

Geraniaceae weeds: a Geranium carolinense, Erodium cicutarium, Erodium *moschatum*

Euphorbiaceae weeds: *Euphorbia helioscopia, Euphorbia maculata, Euphorbia humistrata, Euphorbia esula, Euphorbia heterophylla, Euphorbia brasiliensis, Acalypha australis,* Croton glandulosus, Croton *lobatus, Phyllanthus corcovadensis, Ricinus communis*

Malvaceae weeds: *Abutilon theophrasti, Sida rhombifolia, Sida cordifolia, Sida spinosa, Sida glaziovii, Sida santaremnensis, Hibiscus trionum, Anoda cristata,* Malvastrum coromandelianum Sterculiaceae weeds: Waltheria indica Violaceae weeds: Viola *arvensis,* Viola tricolor Cucurbitaceae weeds: Sicyos *angulatus, Echinocystis lobata, Momordica charantia*

Lythraceae weeds: *Lythrum salicaria*

Apiaceae weeds: Hydrocotyle sibthorpioides, *Oenanthe javanica*

Sapindaceae weeds: *Cardiospermum halicacabum*

Primulaceae weeds: Anagallis *arvensis*

Asclepiadaceae weeds: Asclepias *syriaca, Ampelamus albidus*

Rubiaceae weeds: *Galium aparine, Galium spurium* var. echinospermon, Spermacoce *latifolia, Richardia brasiliensis, Richardia scabra, Borreria alata*

Convolvulaceae weeds: *Ipomoea nil, Ipomoea hederacea, Ipomoea purpurea, Ipomoea hederacea* var. integriuscula, *Ipomoea lacunosa, Ipomoea triloba, Ipomoea acuminata, Ipomoea hederifolia, Ipomoea coccinea, Ipomoea quamoclit, Ipomoea grandifolia, Ipomoea aristolochiaefolia, Ipomoea cairica, Convolvulus arvensis, Calystegia hederacea, Calystegia japonica, Merremia hederacea, Merremia aegyptia, Merremia cissoides,* Jacquemontia tamnifolia Boraginaceae weeds: *Myosotis arvensis*

Lamiaceae weeds: *Lamium purpureum, Lamium amplexicaule,* Leonotis nepetaefolia, *Hyptis suaveolens, Hyptis lophanta, Leonurus sibiricus, Stachys arvensis*

Solanaceae weeds: *Datura stramonium, Solanum nigrum, Solanum americanum, Solanum ptycanthum, Solanum sarrachoides, Solanum rostratum, Solanum aculeatissimum, Solanum sisymbriifolium, Solanum* carolinense, Physalis *angulata,* Physalis subglabrata, Nicandra physalodes Scrophulariaceae weeds: *Veronica* hederaefolia, *Veronica persica, Veronica arvensis*)

Plantaginaceae weeds: *Plantago asiatica, Plantago major, Plantago lanceolata.*

Asteraceae weeds: *Xanthium pensylvanicum, Xanthium occidentale, Helianthus annuus, Matricaria chamomilla, Matricaria perforata, Chrysanthemum segetum, Matricaria matricarioides, Artemisia princeps, Artemisia vulgaris, Artemisia verlotorum,* Solidago *altissima, Taraxacum officinale, Galinsoga ciliata, Galinsoga parviflora, Senecio vulgaris, Senecio brasiliensis, Senecio grisebachii, Conyza sumatrensis, Conyza bonariensis, Conyza canadensis, Ambrosia artemisiaefolia, Ambrosia trifida, Bidens pilosa, Bidens frondosa, Bidens subalternans, Cirsium arvense, Cirsium vulgare, Silybum marianum, Carduus nutans, Lactuca serriola, Sonchus oleraceus, Sonchus asper, Wedelia glauca, Melampodium perfoliatum, Emilia sonchifolia, Tagetes minuta, Blainvillea latifolia, Tridax procumbens,* Porophyllum ruderale, *Acanthospermum australe, Acanthospermum hispidum, Cardiospermum halicacabum, Ageratum conyzoides, Eupatorium perfoliatum,* Eclipta alba, Erechtites hieracifolia, Gamochaeta *spicata, Gnaphalium spicatum, Jaegeria hirta, Parthenium* hysterophorus, Siegesbeckia *orientalis, Soliva sessilis*

Liliaceae weeds: *Allium canadense, Allium* vineale

Commelinaceae weeds: *Commelina communis, Commelina benghalensis, Commelina erecta*

Poaceae weeds: *Echinochloa crus-galli, Echinochloa colonum, Echinochloa phyllopogon, Setaria viridis, Setaria faberi, Setaria glauca, Setaria geniculata, Digitaria ciliaris, Digitaria sanguinalis, Digitaria horizontalis, Digitaria insularis, Eleusine indica, Poa annua, Alopecurus aequalis, Alopecurus myosuroides, Avena fatua, Sorghum halepense, Sorghum vulgare, Agropyron repens, Lolium multiflorum, Lolium perenne, Lolium rigidum, Bromus secalinus, Bromus tectorum, Hordeum jubatum, Aegilops cylindrica, Phalaris arundinacea, Phalaris minor, Apera spica-venti, Panicum dichotomiflorum, Panicum texanum, Panicum maximum, Brachiaria platyphylla, Brachiaria ruziziensis, Brachiaria plantaginea, Brachiaria decumbens, Brachiaria brizantha, Brachiaria* humidicola, *Cenchrus echinatus, Cenchrus pauciflorus, Eriochloa villosa, Pennisetum setosum, Chloris gayana, Chloris virgata, Eragrostis pilosa, Rhynchelytrum repens, Dactyloctenium aegyptium, Ischaemum rugosum, Oryza fatua, Paspalum notatum, Paspalum maritimum, Pennisetum clandestinum, Pennisetum setosum, Rottboellia cochinchinensis*

Cyperaceae weeds: *Cyperus* microiria, *Cyperus* iria, *Cyperus odoratus, Cyperus rotundus, Cyperus esculentus, Kyllinga gracillima*

Equisetaceae weeds: *Equisetum arvense, Equisetum palustre,* etc.

In the above weeds, variations within the species are not particularly limited. Namely, the weeds also include any weeds that have a resistance to a specific herbicide. The resistance may be attributed to a mutation at a target site (target site mutations), or may be attributed to any factors other than target site mutation (non-target site mutations). The factors of resistance by non-target site mutations include metabolic enhancement, defective absorption, defective transition, and efflux out of the system, etc. A cause of the metabolic enhancement includes an enhanced activity of metabolic enzymes such as cytochrome P450 monooxygenases (CYP), aryl acylamidases (AAA), esterases and glutathione S-transferase (GST). The efflux out of the system includes the transfer to a vacuole by an ABC transporter. Examples of resistant weeds are as follows.

Glyphosate Resistance:

Examples of target site mutations include a mutation in EPSPS genes causing an amino acid substitution such as Thr102Ile, Pro106Ser, Pro106Ala, and Pro106Leu. In the present invention, glyphosate-resistant *Eleusine indica, Lolium multiflorum, Lolium rigidum, Digitaria insularis, Amaranthus rudis, Amaranthus palmeri,* and *Echinochloa colona* having one or more (for example, a double mutation of Thr102Ile and Pro106Ser) of these mutations are effectively controlled. Another example of a target site mutation is a copy number amplification of EPSPS genes. In the present inventions, glyphosate-resistant *Amaranthus palmeri, Amaranthus rudis,* and *Kochia scoparia* having the gene amplification are effectively controlled. Examples of weeds having non-target-site mutations Includes glyphosate resistant *Conyza canadensis*, *Conyza sumatrensis*, and *Conyza bonariensis* in which an ABC transporter is involved. They are also effectively controlled.

ALS Inhibitor Resistance:

Examples of target site mutations include a mutation in ALS genes causing an amino acid substitution such as Ala122Thr, Ala122Val, Ala122Tyr, Pro197Ser, Pro197His, Pro197Thr, Pro197Arg, Pro197Leu, Pro197Gln, Pro197Ala, Pro197Ile, Ala205Val, Ala205Phe, Asp376Glu, Asp376Gln, Asp376Asn, Arg377His, Trp574Leu, Trp574Gly, Trp574Met, Ser653Thr, Ser653Asn, Ser635Ile, Gly654Glu and Gly645Asp. In the present invention, ALS inhibitor resistant *Amaranthus retroflexus*, *Amaranthus palmeri*, *Amaranthus hybridus*, *Amaranthus rudis*, *Kochia scoparia* having one or more of these mutations are effectively controlled. Examples of weeds having non-target-site mutations Include ALS inhibitor resistant weeds in which CYP or GST is involved. These weeds include *Lolium rigidum* having enhanced CYP81A10 or CYP81A1v1, *Echinochloa phyllopogon* having enhanced CYP81A12 or CYP81A21, and *Alopecurus myosuroides* having enhanced GSTF1 or GSTU2. They are also effectively controlled.

ACCase Inhibitor Resistance

Examples of target site mutations include a mutation in ACCase genes causing an amino acid substitution such as Ile1781Leu, Ile1781Val, Ile1781Thr, Trp1999Cys, Trp1999Leu, Ala2004Val, Trp2027Cys, Ile2041Asn, Ile2041Val, Asp2078Gly, Cys2088Arg, and Gly2096Ala. In the present invention, ACCase inhibitor resistant *Alopecurus myosuroides*, *Lolium multiflorum*, and *Lolium rigidum* having one or more of these mutations are effectively controlled. Examples of weeds having non-target-site mutations include ACCase inhibitor resistant weeds in which CYP or GST is involved. These weeds include *Lolium rigidum* having enhanced CYP81A10 or CYP81A1v1, *Echinochloa phyllopogon* having enhanced CYP81A12 or CYP81A21, and *Alopecurus myosuroides* having enhanced GSTF1 or GSTU2. They are also effectively controlled.

PPO Inhibitor Resistance:

Examples of target site mutations include a mutation in PPO genes causing an amino acid substitution such as Arg128Leu, Arg128Met, Arg128Gly, Arg128His, Gly210 deletion, Gly114Glu, Ser149Ile, Gly399Ala, and Ala212Thr. Though a weed species usually has two PPO genes such as PPO1 and PPO2, the said mutation may occur in either of PPO1 and PPO2, or both of them, but preferably in PPO 2. In the present invention, PPO inhibitor resistant *Amaranthus palmeri*, *Amaranthus rudis*, *Ambrosia artemisiaefolia*, *Lolium rigidum*, and *Euphorbia heterophylla* having one or more of these mutations are effectively controlled. Examples of weeds having non-target-site mutations include PPO inhibitor resistant *Amaranthus palmeri* and *Amaranthus rudis* in which CYP or GST is involved. They are also effectively controlled.

Auxin Type Herbicide Resistance:

Examples of target site mutations include a mutation in the degron regon of AUX/IAA gene causing an amino acid substitution of Gly-Asn. In the present invention, auxin resistant *Kochia scoparia*, *Amaranthus palmeri*, and *Amaranthus* rudishaving the mutation is effectively controlled. Examples of weeds having non-target-site mutations include dicamba resistant *Amaranthus palmeri* and 2,4-D resistant *Amaranthus rudis* in which CYP or GST is involved. They are effectively controlled.

HPPD Inhibitor Resistance:

Examples of weeds having non-target-site mutations include HPPD inhibitor resistant *Amaranthus palmeri* and *Amaranthus rudis* in which CYP or GST is involved. These weed includes *Amaranthus palmeri* having enhanced CYP72A219, CYP81B or CYP81E8. They are effectively controlled.

PS II Inhibitor Resistance:

Examples of target site mutations include a mutation in psbA genes causing an amino acid substitution such as Val219Ile, Ser264Gly, Ser264Alam, and Phe274Val. In the present invention, PS II inhibitor resistant *Amaranthus palmeri* and *Amaranthus rudis* having one or more of these mutations are effectively controlled. Examples of weeds having non-target-site mutations include *Amaranthus palmeri*, *Amaranthus rudis*, and *Lolium rigidum* in which CYP, GST or AAA is involved. These weeds include *Lolium rigidum* having enhanced CYP71R4. They are also effectively controlled.

Glufosinate Resistance:

Examples of target site mutations include a mutation in glutamine synthase gene causing an amino acid substitution of Asp171Asn. In the present invention, glufosinate resistant *Amaranthus rudis* and *Amaranthus palmeri* having the mutation are effectively controlled. Examples of weeds having non-target-site mutations include glufosinate resistant weeds in which CYP or GST is involved. These weeds include *Amaranthus rudis* and *Amaranthus palmeri* having enhanced CYP72A219, CYP81B or CYP81E8. They are also effectively controlled.

The resistant weeds effectively controlled in the present invention may be resistant to two or more of the above 8 groups. An example of the stacked resistant weed is *Amaranthus rudis* that is resistant to PS II inhibitor, HPPD inhibitor, 2,4-D, PPO inhibitor, ALS inhibitor and glyphosate at the same time. The stacking may be due to a combination of target site mutations, non-target site mutations, or a combination of the both.

The present composition or the present compounds may be used in combination with other herbicides or safeners. Examples of the herbicide and the safener which may be combined to the present composition or the present compounds include the following. The herbicides and the safeners can be used by mixing with the present composition or the present compounds before use, or can be used by incorporated in the present composition in advance.

Herbicide: 2,3,6-TBA, 2,3,6-TBA-dimethylammonium, 2,3,6-TBA-lithium, 2,3,6-TBA-potassium, 2,3,6-TBA-sodium, 2,4-D, 2,4-D-choline, 2,4-D-biproamine, 2,4-D-doboxyl, 2,4-D-2-ethylhexyl, 2,4-D-3-butoxypropyl, 2,4-D-ammonium, 2,4-D-butotyl, 2,4-D-butyl, 2,4-D-diethylammonium, 2,4-D-dimethylammonium, 2,4-D-diolamine, 2,4-D-dodecylammonium, 2,4-D-ethyl, 2,4-D-heptylammonium, 2,4-D-isobutyl, 2,4-D-isooctyl, 2,4-D-isopropyl, 2,4-D-isopropylammonium, 2,4-D-lithium, 2,4-D-meptyl, 2,4-D-methyl, 2,4-D-octyl, 2,4-D-pentyl, 2,4-D-propyl, 2,4-D-sodium, 2,4-D-tefuryl, 2,4-D-tetradecylammonium, 2,4-D-triethylammonium, 2,4-D-tris (2-hydroxypropyl)ammonium, 2,4-D-trolamine, 2,4-DB, 2,4-DB-choline, 2,4-DB-biproamine, 2,4-DB-butyl, 2,4-DB-dimethylammonium, 2,4-DB-isoctyl, 2,4-DB-potassium, 2,4-DB-sodium, acetochlor, ACN (2-amino-3-chloronaphthalene-1,4-dione), alachlor, allidochlor, alloxydim, ametryn, amicarbazone, amidosulfuron, aminocyclopyrachlor, aminocyclopyrachlor-methyl, aminocyclopyrachlor-potassium, aminopyralid, aminopyralid-choline, aminopyralid-potassium, aminopyralid-tripromine, amiprophos-methyl, amitrole, anilofos, asulam, atrazine, azimsulfuron, beflubutamid, benazolin-ethyl, benfluralin, benfuresate, bensulfuron, bensulfuron-methyl, bensulide, bentazon, benthiocarb, benzobicyclonm, benzofenap, benzthiazuro, bialafos, bicyclopyrone, bispyribac, bispyribac-sodium, bixlozone, bromacil, bromobutide, bromofenoxim, bromoxynil, bromoxynil-octanoate, butachlor, butamifos, butralin, butroxydim, butylate, cafenstrole, carbetamide, chloramben, chloridazon, chlorimuron, chlorimuron-ethyl, chlorobromuron, chlorotoluron, chloroxuron, chlorpropham, chlorsulfuron, chlorthal-dimethyl, chlorthiamid, cinmethylin, cinosulfuron, clethodim, clodinafop, clodinafop-propargyl, clomazone, clomeprop, clopyralid, clopyralid-choline, clopyralid-methyl, clopyralid-olamine, clopyralid-potassium, clopyralid-tris(2-hydroxypropyl)ammonium), cloransulam, cloransulam-methyl, cumyluron, cyanazine, cycloate, cyclopyrimorate, cyclosulfamuron, cycloxydim, cyhalofop, cyhalofop-butyl, daimuron, dalapon, dazomet, desmedipham, desmetryn, di-allate, dicamba, dicamba-choline, dicamba-biproamine, dicamba-trolamine, dicamba-diglycolamine, dicamba-dimethylammonium, dicamba-diolamine, dicamba-isopropylammonium, dicamba-methyl, dicamba-olamine, dicamba-potassium, dicamba-sodium, dichlobenil, dichlorprop, dichlorprop-choline, dichlorprop-biproamine, dicamba-tetrabutylammonium, dicamba-tetrabutylphosphonium, dichlorprop-2-ethylhexyl, dichlorprop-butotyl, dichlorprop-dimethylammonium, dichlorprop-ethylammonium, dichlorprop-isoctyl, dichlorprop-methyl, dichlorprop-P, dichlorprop-P-choline, dichlorprop-P-biproamine, dichlorprop-P-2-ethylhexyl, dichlorprop-P-dimethylammonium, dichlorprop-potassium, dichlorprop-sodium, diclofop, diclofop-methyl, diclosulam, difenoxuron, difenzoquat, difenzoquat metilsulfate, diflufenican, diflufenzopyr, diflufenzopyr-sodium, dimefuron, dimepiperate, dimethachlor, dimethametryn, dimethenamid, dimethenamid-P, dimepiperate, dinitramine, dinoseb, dinoterb, diphenamid, diquat, diquat-dibromide, DSMA(disodium methylarsonate), dithiopyr, diuron, DNOC(2-methyl-4,6-dinitrophenol), esprocarb, ethalfluralin, ethametsulfuron, ethametsulfuron-methyl, ethidimuron, ethofumesate, thoxysulfuron, etobenzanid, fenoxaprop, fenoxaprop-ethyl, fenoxaprop-P, fenoxaprop-P-ethyl, fenoxasulfone, fenquinotrione, fentrazamide, fenuron, flamprop-M, flazasulfuron, florasulam, florpyrauxifen, florpyrauxifen-benzyl, fluazifop, fluazifop-butyl, fluazifop-P, fluazifop-P-butyl, flucarbazone, flucarbazone-sodium, flucetosulfuron, flufenacet, flumetsulam, flumetsulam, fluometuron, flupoxam, flupropanate, flupyrsulfuron, flupyrsulfuron-methyl-sodium, flurenol, fluridone, flurochloridone, fluroxypyr, fluroxypyr-butometyl, fluroxypyr-meptyl, flurtamone, foramsulfuron, fosamine, glyphosate, glyphosate-choline, glyphosate-isopropylamine, glyphosate-biproamine, glyphosate-ammonium, glyphosate-diammonium, glyphosate-potassium, glyphosate-sodium, glyphosate-trimesium, halauxifen, halauxifen-methyl, halosafen, halosulfuron, halosulfuron-methyl, haloxyfop, haloxyfop-etotyl, haloxyfop-methyl, haloxyfop-P, haloxyfop-P-etotyl, haloxyfop-P-methyl, hexazinone, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazethapyr, imazethapyr-ammonium, imazosulfuron, indanofan, indaziflam, iodosulfuron, iodosulfuron-methyl-sodium, iofensulfuron, iofensulfuron-sodium, ioxynil, ioxynil-octanoate, ipfencarbazone, isoproturon, isouron, isoxaben, isoxachlortole, isoxaflutole, lenacil, linuron, maleic hydrazide, MCPA(2-(4-chloro-2-methylphenoxy)acetic acid), MCPA-cholin, MCPA-biproamine, MCPA-etexyl, MCPA-butotyl, MCPA-butyl, MCPA-dimethylammonium, MCPA-diolamine, MCPA-ethyl, MCPA-isobutyl, MCPA-isoctyl, MCPA-isopropyl, MCPA-methyl, MCPA-olamine, MCPA-sodium, MCPA-trolamine, MCPB (4-(4-chloro-2-methylphenoxy)butanoic acid), MCPB-choline, MCPB-biproamine, MCPB-ethyl, MCPB-methyl, MCPB-sodium, mecoprop, mecoprop-choline, mecoprop-biproamine, mecoprop-2-ethylhexyl, mecoprop-dimethylammonium, mecoprop-diolamine, mecoprop-ethadyl, mecoprop-isoctyl, mecoprop-methyl, mecoprop-potassium, mecoprop-sodium, mecoprop-trolamine, mecoprop-P, mecoprop-P-choline, mecoprop-P-2-ethylhexyl, mecoprop-P-dimethylammonium, mecoprop-P-isobutyl, mecoprop-P-potassium, mefenacet, mesosulfuron, mesosulfuron-methyl, mesotrione, metam, metamifop, metamitron, metazachlor, metazosulfuron, methabenzthiazuron, methiozolin, methyldymron, metobromuron, metolachlor, metosulam, metoxuron, metribuzin, metsulfuron, metsulfuron-methyl, molinate, monolinuron, naproanilide, napropamide, napropamide-M, naptalam, neburon, nicosulfuron, norflurazon, oleic acid, orbencarb, orthosulfamuron, oryzalin, oxadiargyl, oxadiazon, oxasulfuron, oxaziclomefone, oxyfluorfen, paraquat, paraquat-dichloride, pebulate, pelargonic acid, pendimethalin, penoxsulam, pentanchlor, pethoxamid, phenisopham, phenmedipham, picloram, picolinafen, pinoxaden, piperophos, pretilachlor, primisulfuron, primisulfuron-methyl, prodiamine, profoxydim, prometon, prometryn, propachlor, propanil, propaquizafop, propazine, propham, propisochlor, propoxycarbazone, propoxycarbazone-sodium, propyrisulfuron, propyzamide, prosulfocarb, prosulfuron, pyraclonil, pyrasulfotole, pyrazolynate, pyrazosulfuron, pyrazosulfuron-ethyl, pyrazoxyfen, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quizalofop, quizalofop-ethyl, quizalofop-tefuryl, quizalofop-P, quizalofop-P-ethyl, quizalofop-P-tefuryl, rimsulfuron, saflufenacil, sethoxydim, EPTC(S-ethyl N,N-dipropylcarbamothioate), siduron, simazine, simetryn, S-metolachlor, MSMA(sodium hydrogen methylarsonate), sulcotrione, sulfometuron, sulfometuron-methyl, TCA-ethadyl, sulfosulfuron, swep, TCA(2,2,2-trichloroacetic acid), tebutam, tebuthiuron, tefuryltrione, tembotrione, tepraloxydim, terbacil, terbumeton, terbuthylazine, terbutryn, tetflupyrolimet, thaxtomin A, thenylchlor, thiazopyr, thidiazimin, thiencarbazone, thiencarbazone-methyl, thifensulfuron, thifensulfuron-methyl, tiocarbazil, tolpyralate, topramezone, tralkoxydim, triafamone, tri-allate, triasulfuron, triaziflam, tribenuron, tribenuron-methyl, triclopyr, triclopyr-butotyl, triclopyr-ethyl, triclopyr-triethylammonium, tridiphane, trietazine, trifloxysulfuron, trifloxysulfuron-sodium, trifludimoxazin, trifluralin, triflusulfuron, triflusulfuron-methyl, tritosulfuron, vernolate.

Safeners: benoxacor, cloquintocet, cloquintocet-mexyl, cyometrinil, cyprosulfamide, dichlormid, dicyclonone, disulfoton, daimuron, fenchlorazole, fenchlorazole-ethyl, fenclorim, flurazole, furilazole, fluxofenim, hexim, isoxadifen, isoxadifen-ethyl, mefenpyr, mefenpyr-ethyl, mefenpyr-diethyl, mephenate, metcamifen, oxabetrinil1,8-naphthalic anhydride, 1,8-octamethylene diamine, AD-67(4-(dichloroacetyl)-1-oxa-4-azaspiro [4.5] decane), CL-304415 (4-carboxy-3,4-dihydro-2H-1-benzopyran-4-acetic acid), CSB (1-bromo-4-[(chloromethyl)sulfonyl]benzene), DKA-24(2,2-dichloro-N-[2-oxo-2-(2-propenylamino)ethyl]-N-(2-propenyl)acetamide), MG191(2-(dichloromethyl)-2-methyl-1,3-dioxolane), MG-838(2-propenyl 1-oxa-4-azaspiro[4.5] decane-4-carbodithioate), PPG-1292(2,2-dichloro-N-(1,3-dioxan-2-ylmethyl)-N-(2-propenyl)acetamide), R-28725(3-

(dichloroacetyl)-2,2-dimethyl-1,3-oxazolidine), R-29148(3-(dichloroacetyl)-2,2,5-trimethyl-1,3-oxazolidine), TI-35 (1-(dichloroacetyl)azepane)

As the herbicide and the safener which can be used in combination with the present composition or the present compounds, glyphosate-potassium, glyphosate-dimethylamine, glyphosate-monoethanolamine, dicamba-biproamine, dicamba-diglycolamine, dicamba-tetrabutylammonium, dicamba-tetrabutylphosphonium, glyphosate-isopropyl ammonium, 2,4-D-choline, s-metolachlor, dimethenamid-P, pendimethalin, metribuzin, flufenacet, nicosulfuron, rimsulfuron, acetochlor, mesotrione, isoxaflutole, chlorimuron-ethyl, thifensulfuron-methyl, cloransulam-methyl, imazethapyr-ammonium, isoxadifen-ethyl, benoxacor, dichlormid, furilazole, cyprosulfamide, mefenpyr-diethyl, and cloquintocet-mexyl are particularly preferable.

Examples of a combination of a PPO inhibitor and glufosinate or its salt are described as follows. The numbers in the parentheses are weight ratios based on the glufosinate-ammonium equivalence.

Saflufenacil+glufosinate-ammonium (1+2,000, 1+20,000, 1+200,000, 1+2,000,000, 1+20,000,000)
Saflufenacil+glufosinate-P-ammonium (1+2,000, 1+20,000, 1+200,000, 1+2,000,000, 1+20,000,000)
Saflufenacil+glufosinate-sodium (1+2,000, 1+20,000, 1+200,000, 1+2,000,000, 1+20,000,000)
Saflufenacil+glufosinate-P-sodium (1+2,000, 1+20,000, 1+200,000, 1+2,000,000, 1+20,000,000)
Trifludimoxazin+glufosinate-ammonium (1+2,000, 1+20,000, 1+200,000, 1+2,000,000, 1+20,000,000)
Trifludimoxazin glufosinate-P-ammonium (1+2,000, 1+20,000, 1+200,000, 1+2,000,000, 1+20,000,001)
Trifludimoxazin+glufosinate-sodium (1+2,000, 1+20,000, 1+200,000, 1+2,000,000, 1+20,000,002)
Trifludimoxazin+glufosinate-P-sodium (1+2,000, 1+20,000, 1+200,000, 1+2,000,000, 1+20,000,003)
Flumioxazin+glufosinate-ammonium (1+2,000, 1+20,000, 1+200,000, 1+2,000,000, 1+20,000,000)
Flumioxazin+glufosinate-P-ammonium (1+2,000, 1+20,000, 1+200,000, 1+2,000,000, 1+20,000,000)
Flumioxazin+glufosinate-sodium (1+2,000, 1+20,000, 1+200,000, 1+2,000,000, 1+20,000,000)
Flumioxazin+glufosinate-P-sodium (1+2,000, 1+20,000, 1+200,000, 1+2,000,000, 1+20,000,000)
Compound X+glufosinate-ammonium (1+2,000, 1+20,000, 1+200,000, 1+2,000,000, 1+20,000,000)
Compound X+glufosinate-P-ammonium (1+2,000, 1+20,000, 1+200,000, 1+2,000,000, 1+20,000,000)
Compound X+glufosinate-sodium (1+2,000, 1+20,000, 1+200,000, 1+2,000,000, 1+20,000,000)
Compound X+glufosinate-P-sodium (1+2,000, 1+20,000, 1+200,000, 1+2,000,000, 1+20,000,000)
Lactofen+glufosinate-ammonium (1+2,000, 1+20,000, 1+200,000, 1+2,000,000, 1+20,000,000)
Lactofen+glufosinate-P-ammonium (1+2,000, 1+20,000, 1+200,000, 1+2,000,000, 1+20,000,000)
Lactofen+glufosinate-sodium (1+2,000, 1+20,000, 1+200,000, 1+2,000,000, 1+20,000,000)
Lactofen+glufosinate-P-sodium (1+2,000, 1+20,000, 1+200,000, 1+2,000,000, 1+20,000,000)
Sulfentrazone+glufosinate-ammonium (1+2,000, 1+20,000, 1+200,000, 1+2,000,000, 1+20,000,000)
Sulfentrazone+glufosinate-P-ammonium (1+2,000, 1+20,000, 1+200,000, 1+2,000,000, 1+20,000,000)
Sulfentrazone+glufosinate-sodium (1+2,000, 1+20,000, 1+200,000, 1+2,000,000, 1+20,000,000)
Sulfentrazone+glufosinate-P-sodium (1+2,000, 1+20,000, 1+200,000, 1+2,000,000, 1+20,000,000)
Fomesafen-sodium+glufosinate-ammonium (1+2,000, 1+20,000, 1+200,000, 1+2,000,000, 1+20,000,000)
Fomesafen-sodium+glufosinate-P-ammonium (1+2,000, 1+20,000, 1+200,000, 1+2,000,000, 1+20,000,000)
Fomesafen-sodium+glufosinate-sodium (1+2,000, 1+20,000, 1+200,000, 1+2,000,000, 1+20,000,000)
Fomesafen-sodium+glufosinate-P-sodium (1+2,000, 1+20,000, 1+200,000, 1+2,000,000, 1+20,000,000)
Fluthiacet-methyl+glufosinate-ammonium (1+2,000, 1+20,000, 1+200,000, 1+2,000,000, 1+20,000,000)
Fluthiacet-methyl+glufosinate-P-ammonium (1+2,000, 1+20,000, 1+200,000, 1+2,000,000, 1+20,000,000)
Fluthiacet-methyl+glufosinate-sodium (1+2,000, 1+20,000, 1+200,000, 1+2,000,000, 1+20,000,000)
Fluthiacet-methyl+glufosinate-P-sodium (1+2,000, 1+20,000, 1+200,000, 1+2,000,000, 1+20,000,000)
Carfentrazone-ethyl+glufosinate-ammonium (1+2,000, 1+20,000, 1+200,000, 1+2,000,000, 1+20,000,000)
Carfentrazone-ethyl+glufosinate-P-ammonium (1+2,000, 1+20,000, 1+200,000, 1+2,000,000, 1+20,000,029)
Carfentrazone-ethyl glufosinate-sodium (1+2,000, 1+20,000, 1+200,000, 1+2,000,000, 1+20,000,000)
Carfentrazone-ethyl+glufosinate-P-sodium (1+2,000, 1+20,000, 1+200,000, 1+2,000,000, 1+20,000,000)

The cultivation of crops in the present invention can be managed according to the plant-nutrition in the common crop cultivation. The fertilization system may be based on Precision Agriculture adopting variable rate application or may be conventionally uniform one.

EXAMPLES

Example 1

An aqueous dilution of glufosinate-ammonium was prepared by mixing a predetermined amount of a commercial glufosinate-ammonium formulation (manufactured by Bayer Cropscience KK under the trade name of Basta) with water so as to have a concentration of 20,000 ppm of glufosinate-ammonium. An aqueous dilution of trifludimoxazin was prepared by mixing one part of a trifludimoxazin formulation (obtained by mixing a predetermined amount of trifludimoxazin with acetone containing 2% of Tween 20) with 4 parts of water, so as to have a concentration of 10 ppm of trifludimoxazin. An aqueous dilution of saflufenacil was prepared by replacing aforementioned trifludimoxazin with a commercial saflufenacil formulation (manufactured by BASF crop protection under the trade name of Sharpen) so as to have a concentration of 10 ppm of saflufenacil.

One droplet of the glufosinate-ammonium dilution having 2 micro liter was spotted on the $2^{nd}$ leaf of a corn plant at the stage of 2.5-leaf. In the mixture treatment, a droplet of the PPO inhibitor dilution having 2 micro liter was subsequently put on the glufosinate-ammonium droplet.

3 days after the spot-on treatments, the injured area of the treated leaf was visually estimated as a percentage on the total area of the treated leaf. The results are shown in Table 1. As shown in Table 1, glufosinate crop injury was drastically reduced by an addition of a PPO inhibitor at the weight ratio of 1/2,000.

TABLE 1

| Glufosinate-ammonium | PPO inhibitor | Injured leaf area |
|---|---|---|
| 40,000 ng/plant | None | 60% |
| 40,000 ng/plant | Trifludimoxazin 20 ng/plant | 30% |
| 40,000 ng/plant | Saflufeancil 20 ng/plant | 20% |

TABLE 2

| Glufosinate-ammonium | PPO inhibitor | Injured leaf area |
|---|---|---|
| 400,000 ng/plant | None | 70% |
| 400,000 ng/plant | Trifludimoxazin 0.2 ng/plant | 40% |
| 400,000 ng/plant | Saflufeancil 0.2 ng/plant | 20% |

Example 2

An aqueous dilution of trifludimoxazin was prepared by mixing one part of a trifludimoxazin formulation (obtained by mixing a predetermined amount of trifludimoxazin with acetone containing 2% of Tween 20) with 4 parts of water, so as to have a concentration of 0.1 ppm of trifludimoxazin. An aqueous dilution of saflufenacil was prepared by replacing aforementioned trifludimoxazin with a commercial saflufenacil formulation (manufactured by BASF crop protection under the trade name of Sharpen) so as to have a concentration of 0.1 ppm of saflufenacil.

One droplet having 2 micro liter of a commercial formulation of glufosinate-ammonium (manufactured by Bayer Cropscience KK under the trade name of Basta) having 200,000 ppm (200 g/L) of glufosinate-ammonium was spotted on the $2^{nd}$ trifoliate leaf of a soybean plant at the stage of 2 trifoliate leaf. In the mixture treatment, a droplet of the PPO inhibitor dilution having 2 micro liter was subsequently put on the droplet of glufosinate-ammonium.

6 days after the spot-on treatments, the injured area of the treated leaf was visually estimated as a percentage on the total area of the treated leaf. The results are shown in Table 2. As shown in Table 2, glufosinate crop injury was drastically reduced by an addition of a PPO inhibitor at the weight ratio of 1/2,000,000.

INDUSTRIAL APPLICABILITY

The herbicidal composition of the present invention can effectively control weeds with reduced crop injury.

The invention claimed is:

1. A herbicidal composition comprising a PPO inhibitor and glufosinate or its salt, wherein the weight ratio of the PPO inhibitor to glufosinate or its salt is from 1/20,000,000 to 1/2,000,
    wherein the PPO inhibitor is saflufenacil or trifludimoxazin.

2. The herbicidal composition according to claim 1, wherein the weight ratio of the PPO inhibitor to glufosinate or its salt is from 1/2,000,000 to 1/2,000.

3. A method for controlling weeds in a crop field comprising a step of applying a PPO inhibitor and glufosinate or its salt to the weeds or a soil of the place where the weeds are growing or will grow, wherein the weight ratio of the PPO inhibitor to glufosinate or its salt is from 1/20,000,000 to 1/2,000,
    wherein the PPO inhibitor is saflufenacil or trifludimoxazin.

4. The method according to claim 3, wherein the weight ratio of the PPO inhibitor to glufosinate or its salt is from 1/2,000,000 to 1/2,000.

* * * * *